US012383179B2

(12) United States Patent
Davis et al.

(10) Patent No.: US 12,383,179 B2
(45) Date of Patent: Aug. 12, 2025

(54) DATA PROCESSING SYSTEM FOR DETECTING HEALTH RISKS AND CAUSING TREATMENT RESPONSIVE TO THE DETECTION

(71) Applicant: Carnegie Mellon University, Pittsburgh, PA (US)

(72) Inventors: Alexander Davis, Pittsburgh, PA (US); Tamar Priya Krishnamurti, Pittsburgh, PA (US); Kristen Allen, Pittsburgh, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 879 days.

(21) Appl. No.: 17/277,863

(22) PCT Filed: Sep. 23, 2019

(86) PCT No.: PCT/US2019/052407
§ 371 (c)(1),
(2) Date: Mar. 19, 2021

(87) PCT Pub. No.: WO2020/061562
PCT Pub. Date: Mar. 26, 2020

(65) Prior Publication Data
US 2021/0345925 A1 Nov. 11, 2021

Related U.S. Application Data

(60) Provisional application No. 62/765,954, filed on Sep. 21, 2018.

(51) Int. Cl.
*A61B 5/16* (2006.01)
*A61B 5/00* (2006.01)
(Continued)

(52) U.S. Cl.
CPC ............ *A61B 5/165* (2013.01); *A61B 5/0022* (2013.01); *A61B 5/150809* (2013.01);
(Continued)

(58) Field of Classification Search
CPC . A61B 5/165; A61B 5/0022; A61B 5/150809; A61B 5/150816;
(Continued)

(56) References Cited

U.S. PATENT DOCUMENTS 11,594,311 B1 * 2/2023 Bradley ................. G06N 20/00
11,682,495 B2 * 6/2023 Krishnamurti ....... A61B 5/7264
705/2

(Continued)

FOREIGN PATENT DOCUMENTS

WO WO-2016057960 A1 * 4/2016 ........... G06T 7/0014
WO WO 2018/071845 4/2018

OTHER PUBLICATIONS

Villa et al., Cluster analysis to estimate the risk of preeclampsia in the high-risk Prediction and Prevention of Preeclampsia and Intrauterine Growth Restriction (PREDO) study, Mar. 28, 2017, PLoS ONE, Issue 3, vol. 12, pp. 1-11. (Year: 2017).*

(Continued)

*Primary Examiner* — Christopher L Gilligan
(74) *Attorney, Agent, or Firm* — Fish & Richardson P.C.

(57) ABSTRACT

A data processing system is configured to identify treatment responsive to a health risk determined from feature data provided by one or more networked data sources. A classification engine generates a feature vector based on a natural language processing (NLP) of input data representing words provided by a user. Features of the feature vector represent health risk factors. Machine learning logic classifies the features to generate a classification metric indicating whether the features are indicative of health risks or not
(Continued)

indicative of health risks. A prediction value is generated indicating a likelihood of each health risk factor for the patient. The patient can be diagnosed with a health condition or disease based on the identified health risks.

20 Claims, 13 Drawing Sheets

(51) Int. Cl.
    *A61B 5/15*     (2006.01)
    *G16H 10/20*     (2018.01)
    *G16H 40/67*     (2018.01)
    *G16H 50/30*     (2018.01)
    *G06F 40/40*     (2020.01)

(52) U.S. Cl.
    CPC .. *A61B 5/150816* (2013.01); *A61B 5/150824* (2013.01); *A61B 5/7275* (2013.01); *A61B 5/7435* (2013.01); *G16H 10/20* (2018.01); *G16H 40/67* (2018.01); *G16H 50/30* (2018.01); *A61B 2560/02* (2013.01); *G06F 40/40* (2020.01)

(58) Field of Classification Search
    CPC ............ A61B 5/150824; A61B 5/7275; A61B 5/7435; A61B 2560/02; A61B 5/486; A61B 5/7475; G16H 10/20; G16H 40/67; G16H 50/30; G06F 40/40; G10L 15/26; G10L 15/18
See application file for complete search history.

(56) References Cited

U.S. PATENT DOCUMENTS

| | | | |
|---|---|---|---|
| 2005/0020903 A1* | 1/2005 | Krishnan | G16H 50/20 600/407 |
| 2016/0004831 A1 | 1/2016 | Carlson et al. | |
| 2016/0314784 A1 | 10/2016 | Kleppe et al. | |
| 2017/0286622 A1 | 10/2017 | Cox et al. | |
| 2018/0025121 A1 | 1/2018 | Fei et al. | |
| 2018/0350451 A1* | 12/2018 | Ohnemus | G16H 40/67 |
| 2019/0074090 A1* | 3/2019 | Ronen | A61B 5/7275 |
| 2020/0005901 A1* | 1/2020 | Cohen | G16H 50/30 |
| 2020/0405225 A1* | 12/2020 | Kennedy | G16H 50/30 |

OTHER PUBLICATIONS

Feller et al., Using Clinical Notes and Natural Language Processing for Automated HIV Risk Assessment, Feb. 1, 2018, Journal of Acquired Immune Deficiency Syndromes, pp. 160-166. (Year: 2018).*
PCT International Preliminary Report on Patentability in International Application No. PCT/US2019/052407, dated Mar. 23, 2021, 6 pages.
Allen et al., ""Showing without telling: Indirect identification of psychosocial risks during and after pregnancy"", PNAS, Aug. 2018, 8 pages.
PCT International Search Report and Written Opinion in International Application No. PCT/US2019/052407, dated Dec. 6, 2019, 6 pages.

* cited by examiner

| Topic 2 Cooking | Topic 3 Childcare | Topic 5 Pregnancy-related expectations | Topic 12 Family relationships | Topic 13 Labour and delivery anticipation | Topic 18 Work-life balance |
|---|---|---|---|---|---|
| dinner | baby | pregnancy | kid | excite | work |
| cry | help | will | older | first | home |
| favourite | husband | pregnant | interact | pretty | feel |
| cook | watch | know | mom | due | leave |
| definate | get | want | newborn | nervous | good |

| Topic 20 [no topic identified] | Topic 27 Feeling overwhelmed | Topic 28 Discomfort | Topic 33 Nurturing | Topic 39 Parental responsibilities | Topic 40 Lack of partner support |
|---|---|---|---|---|---|
| play | time | just | take | little | husband |
| get | spend | emotional | care | baby | sick |
| one | just | uncomfortable | happy | much | help |
| love | overwhelm | physical | nurse | also | morning |
| try | change | put | try | talk | anything |

DATA PROCESSING SYSTEM FOR DETECTING HEALTH RISKS AND CAUSING TREATMENT RESPONSIVE TO THE DETECTION

CLAIM OF PRIORITY

This application is the National Stage Entry of International Patent Application Serial No. PCT/US2019/052407, filed on Sep. 23, 2019, which claims priority under 35 U.S.C. § 119 (e) to U.S. Provisional Application Ser. No. 62/765,954, filed on Sep. 21, 2018, the entire contents of each of which are hereby incorporated by reference.

TECHNICAL FIELD

This application relates to machine learning processes. More specifically, this application describes methods and systems for generating feature data from data received by one or more data sources and processing the feature data to detect a health risk and cause a treatment responsive to the detected health risk.

BACKGROUND

Generally, psychological distress in the form of depression, anxiety, and other mental health issues can have serious consequences for individuals and society. Unfortunately, stigma surrounding poor mental health can prevent disclosure of depression, anxiety, and suicidal ideation (including thoughts of self-harm or harm of close others). For example, perceived stigma and the associated secrecy around mental illness can be positively linked with feelings of hopelessness and suicidal ideation. Generally, the standard practice of clinicians asking people about suicidal thoughts fails in many cases. It has been shown approximately 80% of patients who ultimately died of suicide report no suicidal thoughts when prompted by their general practitioner.

SUMMARY

Quick, accurate, and indirect detection of health risks accelerates the discovery and treatment of medical issues as they arise. For example, diseases such as preeclampsia and gestational diabetes can be more easily identified if the associated risk factors are detected early during pregnancy. In another example, detection of psychosocial risk factors for a patient can help a medical service provider determine that the patient has anxiety, depression, or may be experiencing intimate partner violence. Regarding depression, during pregnancy approximately 15% of women report experiencing depression, and more than 10% of women report experiencing depression in the year following birth. These rates reflect the incidence of depression actually captured by healthcare providers. However, because social stigma surrounding depression is a barrier to disclosure, depression and other mental health conditions are likely even more common during this time than is currently documented. Current predictive psychometric measures of depression are not consistently administered at routine care, exacerbating the problem of adequate detection.

Generally, depression, mental health risks, and other risks during pregnancy and the postpartum period (including early postpartum—6-8 weeks after delivery to late postpartum— up to one year after delivery) are treatable but underdiagnosed conditions. These risks are associated with adverse birth outcomes, including low birth weight and preterm birth. Effective treatment strategies are available during the peripartum period, for example, including safe antidepressant medications and cognitive behavioral therapy. Generally, a failure to identify these risks can result in a failure to apply an associated treatment. Identifying the onset of medical health risks earlier than current methods provide has the potential to significantly improve detection and early treatment, especially among those groups less likely to actively disclose risk factors or seek care. Gathering data about these health risks in a non-medical setting can facilitate detection of these health risks and the associated treatment.

There is a need to supplement traditional methods for evaluating suicidality, depression, and other psychosocial health risks that minimizes the need for direct disclosure from the individual. The data processing system described in this document is configured to detect health risks in patients and cause treatment responsive to the detection. The data processing system is configured to receive feature data from one or more networked data sources. The feature data includes one or more features that can indicate the health risks a patient is experiencing. The data processing system is configured to detect the features in the feature data and determine from the detected features which health risks the patient is experiencing.

The data processing system is configured to determine which features are indicative of which health risks. The data processing system can be trained with training data that associates (or classifies) health risks with features of the feature data. The data processing system can update the classifications over time as more feature data are received from the one or more network sources.

The implementations described herein can provide various technical benefits. For instance, the techniques described herein enable the data processing system to gather feature data in a non-invasive, non-medical environment. A patient is more likely to provide more candid feature data when the data are collected in a non-invasive way and/or when the feature data are gathered in a non-medical environment. The data processing system enables such a collection by extracting features from language data using natural language processing (NLP) through a personal data collection device (e.g. smartphone, website). The data processing system is configured to generate features and data dictionaries each including a plurality of words and/or phrases that indicate one or more health risk factors. The data processing system is configured to determine that the health risk factors are present in the patient and subsequently determine what treatment can be applied to avoid adverse health outcomes, such as self-harm or harm of close others resulting from depression, to treat disease, such as gestational diabetes, and to detect and stop other health risks, such as intimate partner violence or non-violent abuse.

In an aspect, a data processing system is configured to identify treatment responsive to a health risk determined from feature data provided by one or more networked data sources. The data processing system includes a classification engine that generates a feature vector based on a natural language processing (NLP) of input data representing one or more words provided by a user, with the feature vector including one or more features representing one or more health risk factors. The classification engine classifies, using machine learning logic, each of the one or more features of the feature vector to generate a classification metric indicating, for each of the one or more features, that the feature is indicative of a health risk or not indicative of a health risk. The data processing system includes a prediction engine that generates a prediction value indicative of a predicted likelihood of each health risk factor of the one or more health risk factor. The prediction engine assigns, to one or more of the classification metrics, a prediction weight, and determines the prediction value for each health risk factor based on the assigned prediction weights.

In some implementations, the data processing system includes a display engine that generates data for a graphical user interface configured for displaying, when rendered on a client device, one or more prompts to enter the input data, the prompts including open-ended queries. In some implementations, the graphical user interface is configured to display a determined health condition for the user determined by comparing prediction values for one or more of the health risk factors to threshold values. In some implementations, the data processing system includes a display engine configured to generate data for a graphical user interface including a user status report, where data for the graphical user interface is transmittable to a remote device for review by a medical service provider.

Generally, the natural language processing is used to generate the features for risk classification a feature of the feature vector represents a demographic of the user and other user-specific data the prediction engine is configured to select a health condition for a user in response to a given prediction value for a given health risk factor exceeding a threshold value.

In some implementations, the health risks include one or more mental and behavioral health risks including a risk of depression, a risk of suicidality, a risk of self-harm, a risk of harm from others including intimate partner violence, and a risk of an addiction. In some implementations, the input data comprises audio data received through a microphone.

In an aspect, a method for identifying treatment responsive to a health risk determined from feature data provided by one or more networked data sources includes generating a feature vector based on a natural language processing (NLP) of input data representing one or more words provided by a user, with the feature vector including one or more features representing one or more health risk factors. The method includes classifying, using machine learning logic, each of the one or more features of the feature vector to generate a classification metric indicating, for each of the one or more features, that the feature is indicative of a health risk or not indicative of a health risk. The method includes assigning, to one or more of the classification metrics, a prediction weight. The method includes determining the prediction value for each health risk factor based on the assigned prediction weights.

In some implementations, the method includes generating data for a graphical user interface configured to display, when rendered on the client device, one or more prompts to enter the input data, the prompts including open-ended queries. In some implementations, the graphical user interface is configured to display a determined health condition for a user determined by comparing prediction values for one or more of the health risk factors to threshold values. In some implementations, the method includes generating data for a graphical user interface including a user status report, where data for the graphical user interface is transmittable to a remote device for review by a medical service provider.

In some implementations, the natural language processing is used to generate features for risk classification a feature of the feature vector represents a demographic of the user and other user-specific data.

In some implementations, the method includes include selecting a health condition for the user in response to a given prediction value for a given health risk factor exceeding a threshold value.

In some implementations, the health risks include one or more mental and behavioral health risks including a risk of depression, a risk of suicidality, a risk of self-harm, a risk of harm from others including intimate partner violence, and a risk of an addiction. In some implementations, the input data comprises audio data received through a microphone.

In an aspect, a non-transitory computer readable medium stores instructions that are executable by one or more processors configured to perform operations that include generating a feature vector based on a natural language processing (NLP) of input data representing one or more words provided by a user, with the feature vector including one or more features representing one or more health risk factors. The operations include classifying, using machine learning logic, each of the one or more features of the feature vector to generate a classification metric indicating, for each of the one or more features, that the feature is indicative of a health risk or not indicative of a health risk. The operations include assigning, to one or more of the classification metrics, a prediction weight. The operations include determining the prediction value for each health risk factor based on the assigned prediction weights. In some implementations, the operations include generating data for a graphical user interface configured to display, when rendered on a client device, one or more prompts to enter the input data, the prompts including open-ended queries.

The details of one or more embodiments are set forth in the accompanying drawings and the description below. Other features and advantages will be apparent from the description and drawings, and from the claims.

BRIEF DESCRIPTION OF THE DRAWINGS

FIG. 3B shows example of topics representing features.

FIGS. 6A-6C show example user interfaces.

DETAILED DESCRIPTION

The apparatus, methods and systems described herein can quickly, accurately, and indirectly detect health risks, accelerating the discovery and treatment of medical issues as they arise. One example of a health risk for which the data processing system can improve detection and subsequent intervention is postpartum depression. The non-invasiveness of the collection of input data (e.g., using journal entries or other such means), which prompt each patient to talk about his or her day, produces more candid responses that reveal potential mental health issues or other health conditions in the patient. The communication of risk to physicians and other providers through an interface allows providers to provision care based on better and quicker data (e.g., received the same day as the risk is experienced by the patient).

Figure 1:
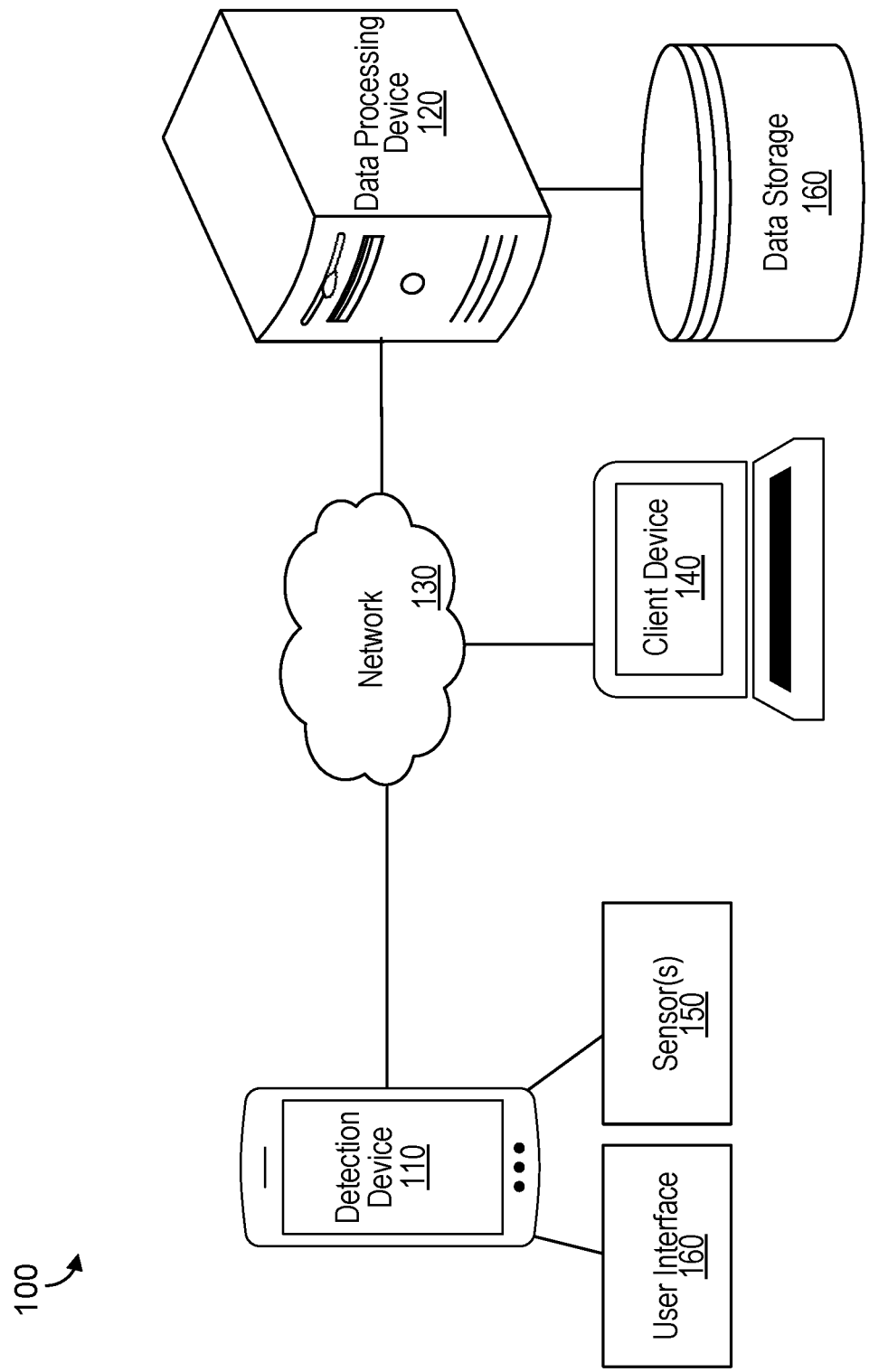
FIG. 1 is a block diagram of an example data processing system.

FIG. 1 is a block diagram of an example computing environment 100 for detecting health risks and causing treatment responsive to the detection. Overall, a detection device 110 is used to collect input data from a source of the input data. The input data can include a speech signal, text data, responses to questionnaires, and so forth. The detection device 110 routes the input data to a data processing device 120 for analysis of the input data and the extraction of features from the input data. The routing can be done, for example, over a wired or wireless network 130. The data processing device 120 is configured to analyze the input to extract one or more features of the input data. The data processing device 120 is configured to provide an output representing one or more health risks experienced by the source of the input data (e.g., a patient that provided the input data). The output can include a visual representation of the identified health risks of the patient. The visual representation can include alerts, alarms, etc. that communicate the detection of the health risks to the patient. In some implementations, the visual representation can include one or more interactive controls that facilitate treatment a condition or diseases associated with the health risks that are detected. For example, the visual representation can include a link to another data source (such as a website), additional prompts for information, a control for contacting a physician, and so forth. The visual representation can be displayed, for example, on a display of a client device 140 to physicians and other healthcare providers. The client device 140 provides output representing one or more health risks experienced by the source of the input data (e.g., a patient that provided the input data) to a clinical service provider, including visual representation of identified health risks, alerts, alarms, and other communications of health risks. The client device may be integrated into an electronic medical record (EMR) and related systems of EMRs.

In some implementations, the detection device 110, data processing device 120, and client device 140 are included in a single computing system, and the functions of these devices can be executed using one or more processors of that computing system.

Generally, the detection device 110 includes a computing device (or plurality of computing devices) for receiving or collecting the input data and converting the input data signal into a representation for processing by the data processing device 120. For example, if a speech signal is recorded, the detection device 110 can convert the speech signal into digital data for processing into feature data by the data processing device 120. The detection device 110 can be in communication with one or more sensors 150 for receiving the input data. For example, text data can be input by a patient using a touchscreen or keyboard responsive to prompts on a user interface 160. For example, a speech signal can be recorded by a sensor 150 such as a microphone and sent to a detection device 110. The microphone can be remote from detection system and can send the speech signal to the detection device 110 over the network 130. In some implementations, the microphone is local to the detection system, and may include data shared from other digital applications such as personal assistant text data (e.g. Siri, Alexa, OK Google). In some implementations, input data sources include natural language data shared with the application from other digital sources. The digital sources can include social media posts, shared group forum text, internet search terms, text messages, SMS or instant messaging data, medical history pulled from EMR, language detected from video diaries, online video uploads, and so forth. The detection device 110 can include a smartphone, laptop, personal computer (PC), or other such computing device. In some implementations, the detection device 110 includes a wearable device configured to record biometric data, which can be included in the feature data. In some implementations, the detection device includes a personal assistant device configured to record the speech signal, and which can be configured to generate audio prompts to the patient for acquiring additional input data.

In some implementations, the input data are collected using a smartphone application between visits with a medical service provider, periods when issues may emerge but go undetected. With this approach, a mobile health application or similar interface is used to solicit a daily journal entry, either verbally through speech recognition software or as a written entry by the patient.

A natural language processing (NLP) engine can be used to parse text received from the patient and identify psychosocial and other health risks. For example, daily journal entries captured using a smartphone application or other similar apparatus can be analyzed via a combination of machine learning and natural language processing, such as topic models and neural networks with word embedding inputs to assess the onset and trajectory of depression during pregnancy and the postpartum period and other health risks. For example, sentiment and topic model outputs combined with mood measures can be used to predict Edinburgh Postnatal Depression Scale (EPDS) scores.

The data processing device 120 can use natural language processing (NLP) and closed-form indirect questions on data collected through an application on a smart phone or similar apparatus to predict health risks such as depression among peripartum women. Patients can be asked open-ended journal questions each day and can respond by text or voice in an application on a smart phone or similar apparatus. Examples of questions are: 1) "How would you describe your overall mood in the past 24 hours? What had the biggest impact on your mood, and why?" 2) "In looking back at the past 24 hours, what events or interactions stand out? How did they make you feel?" and 3) "What activity or event did you most enjoy in the past 24 hours? What did you enjoy the least? Why?"

Generally, the data collection device 110 can use real-time data collection. The input data can be sent to the data processing device 120 for combining with statistical machine learning algorithms, to detect and intervene in health risks such as those during pregnancy, delivering actionable information as part of routine prenatal care through the first three months postpartum. Speed is enabled by daily collection of data on a smartphone application or similar apparatus between prenatal visits and after birth, periods when issues may emerge but go undetected. Accuracy is enabled by analyzing daily journal entries with a combination of the machine learning natural language processing methods described herein. In contrast to unfeasible methods like completing daily (or even weekly) psychometric measures, which could be highly sensitive to changes in depressive symptoms, patients complete daily journals, a fairly common practice that has been shown to improve mental health status on its own. The privacy and control over a journal entry is likely to produce more candid responses that reveal potential mental health issues, while also providing the simultaneous benefit of journaling. The real-time feedback enables women to take treatment-seeking action in the moment.

The data collection device 110 is configured to collect input data such as, baseline demographic information, pregnancy history (e.g., miscarriage, prior preterm birth), conception method (e.g., natural, IVF, ovulation drugs), medical history (e.g., diabetes, hypertension), and behavior (e.g., drugs/tobacco/alcohol). Patients are asked to complete a daily app-based journal as part of routine app use. To remind the patient to complete the daily journal, they will receive a push notification and have the daily journal added to their to-do list in the app. As an example, app-based daily multiple-choice questions ask about mood, sleep, relationship conflict, and fetal movement (after 28 weeks).

Figure 2:
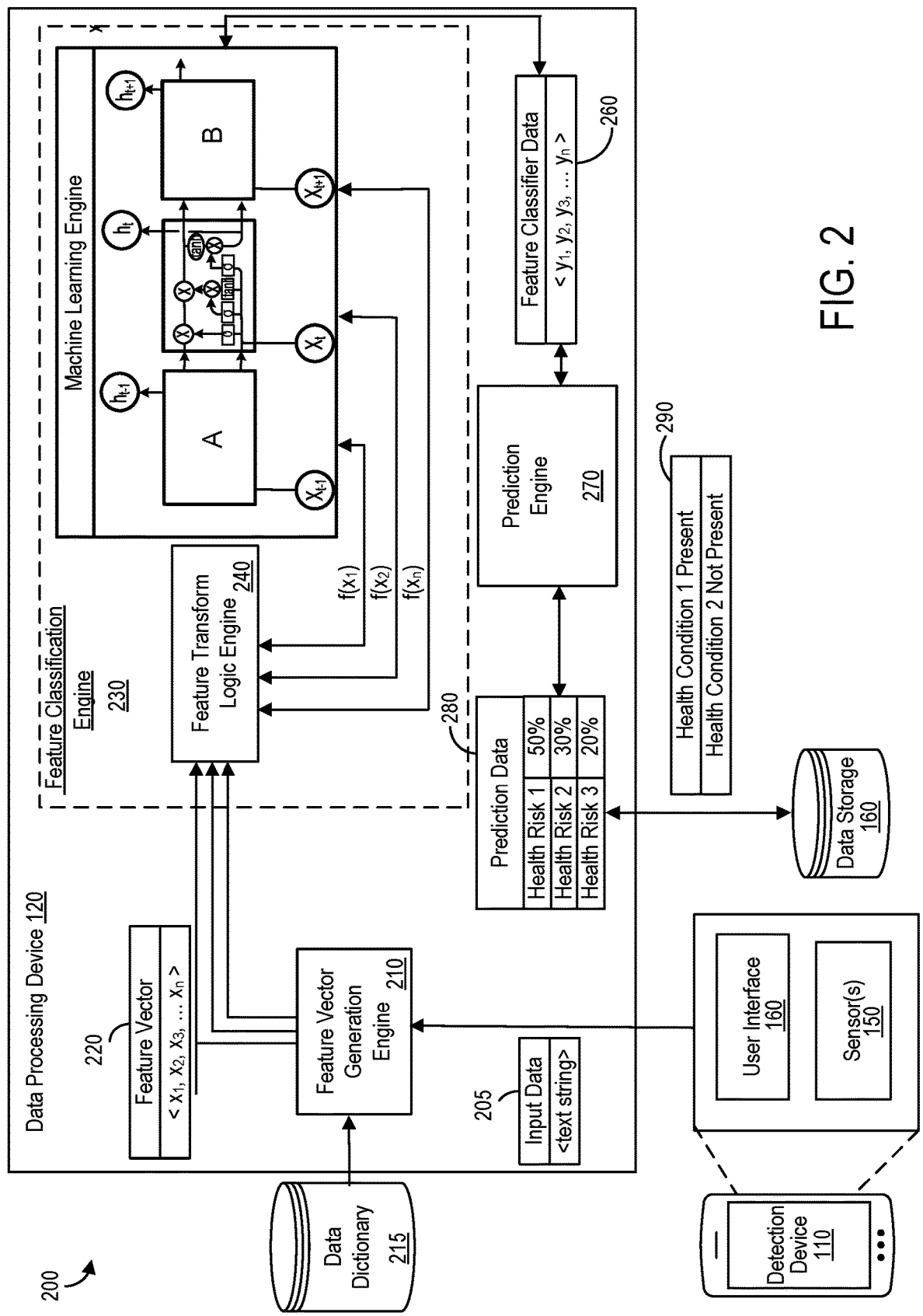
FIG. 2 shows a block diagram of an example of a feature detection device of the data processing system.

Once the input data are received by the data processing device 120, the input data are converted into feature data as described in relation to FIG. 2. The feature data are classified by a feature classification engine of the data processing device 120. The feature classification engine is configured to classify the features as representing one or more health risks. The data processing device 120 can store the results of the classification in a profile associated with the patient, such as in a data storage 160 associated with the data processing device 120.

The results of the classification can be used for a variety of applications, such as facilitating remediation of the health risk. The health risk can be associated with one or more health conditions, such as diseases, mental illness, exposure to intimate partner violence, and so forth. Depending on which health conditions are associated with the detected health risks, the data processing device 120 (or other device of the computing environment 100) can help the patient remediate the condition. For example, a graphical user interface (GUI) can present the patient with options to seek professional assistance. In some implementations, the patient can be presented with a tentative diagnosis to be verified through the client device 140 in collaboration with a clinical provider (e.g., physician). In some implementations, a summary of the health risks can be generated and stored on the client device 140 presented to a health service provider at a later time. That device may have one or more options for the clinical provider to review risk information collected from the data collection device 110 and processed through the data processing device 120. For example, machine learning models that use features from journal entries provided by the patient are used to predict depression risk. Patients meeting a depression risk threshold are flagged as red on the patient status in the client device 140 presented to the clinical provider. Additional alerts based can be presented below the patient status. The data presented to the patient and clinical provider can be in the form of a user interface, alert, push notification, and so forth.

In some implementations, the results of the classification can be used to prompt the patient to provide additional input data. For example, in response to detecting a health risk, the detection device 110 can be configured to generate prompts requesting responses from the patient. In some implementations, the prompts can request that the patient take remedial action (contact a health service provider, link to a local or national organization, or perform some other action).

In some implementations, such as if patient consent is received, the results of the classification can be sent to an identified professional (such as a physician, therapist, or other health service provider etc.) through the client device 140 which can assist the professional with diagnosing the health condition or otherwise assisting the patient. For example, with patient consent, a therapist can be contacted to intervene if a sequence of diary entries of a patient indicate that the patient may engage in self-destructive behavior. In some implementations, the health service provider can be informed of the health risk with an alert, notification, etc.

FIG. 2 shows an example of a data processing system 200. The data processing system 200 in this example includes the detection device 110 and the data processing device 120 of FIG. 1. The data processing system 200 shows the detection device 110 and the data processing device 120 as different computing devices, but the devices can be combined into a single computing device. The data processing device 120 includes feature vector generation engine 210, a classification engine 230 and a prediction engine 270. The feature classification engine 230 and the prediction engine 270 are in communication with each other and with the detection device 110.

The detection device 110 is configured to display the user interface 160 with which patient (or other user) can interact. Examples of the user interface are described in relation to FIGS. 6A-6C. The user interface 160 and/or sensors 150 of the detection device 110 provides receives the input data. The data processing device 120 processes these inputs to determine features (e.g., parameters) that are indicative of the user's interaction with the user interface 160. The detection device 110 stores user data, such as demographic data, etc. which can be input into the feature vector generation engine 210.

The patient can interact with the user interface 160 or provide other input data 205 to the sensors 160 in a variety of ways. For example, the patient can submit journal/diary entries to a journal application. In this way the detection device receives text input from the patient. In some implementations, the patient can speak, and a microphone can record the patient's speech to generate a speech signal. The speech signal can be converted to text using a speech-to-text program to generate additional input data 205. In some implementations, the detection device can provide a questionnaire to the patient and receive responses as input data 205. As described previously, other input mechanisms are possible. The detection device can be configured to scan text messages, record search queries, and obtain other input data 205 generated by the patient with the consent of the patient such as written emails, social media content, internet message board posts, online product reviews, or blog posts. In this way, the detection device can passively gather input data from the patient which can provide more candid information than data obtained in an explicit manner or directly to a medical service provider.

In some implementations, the data processing device 120 is configured to map the topics and sentiments conveyed in natural language journal entries to measures of psychosocial risk using three distinct natural language processing algorithmic approaches. Briefly turning to FIG. 3A, examples of input data 300 are shown, and how the input data 300 are collected and analyzed. Input data 300 shows an example quote taken from a journal entry 310. The entry 310 can be generated by the patient in response to open-ended questions, such as "What events have most impacted your mood in the past 24 hours?" An example response to that question, along with her response to an established psychometric measure of depression (EPDS) are shown in input data 320. Three natural language processing techniques 330 are shown. The NLP techniques 330 include Latent Dirichlet Allocation, capturing the topics of the entry. The NLP techniques 330 include positive and negative sentiment of the words used. The NLP techniques include deep neural network word embeddings. Other NLP techniques can also be applied to the journal entry. Each of those natural language models 330 outputs a score that is entered into a regularized logistic regression model using a LASSO 340 (Least Absolute Shrinkage and Selection Operator) or other prediction method. In the LASSO example 340, it uses cross validation to select natural language factors that best predict EPDS scores.

Figure 3A:
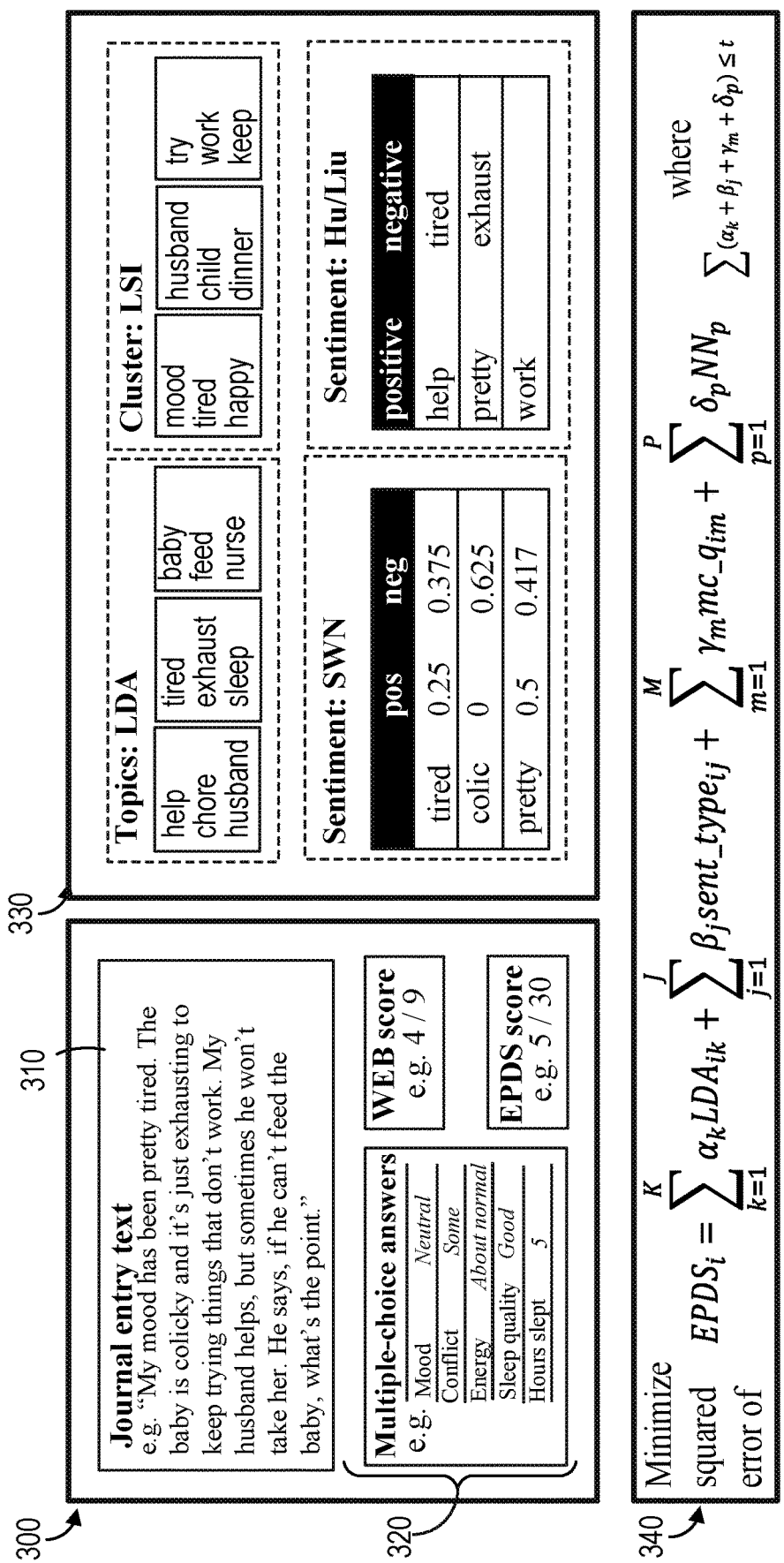
FIG. 3A shows an example of input data and feature selection.

Returning to FIG. 2, the input data 205 are transformed into features of a feature vector 220 by feature vector generation engine 210 (such as using the NLP models described in relation to FIG. 3A). The feature vector 220 concisely represents the characteristics of the input data for the patient. For example, the feature vector can be generated by the feature vector generation engine based on parsing the text of the input date 205 and comparing discovered words in the text to items in one or more data dictionaries 215. A data dictionary can specify words or phrases that correspond to features for including in the feature vector 220.

The feature vector generation engine 210 generates a high-dimensional vector including one or more features that are extracted from the input data. In some implementations, the features can correspond to the words or phrases of the data dictionary 215.

The feature vector 220 is sent from the feature vector generation engine 210 to the feature classification engine 230. The feature classification engine 230 includes logic that transforms the feature vector 220 into data that can be processed by machine learning logic 250. The feature classification engine includes a feature transform logic engine 240 and machine learning engine 250.

Turning briefly to FIG. 3B, feature data 350 is shown. The feature data 350 includes the top five words from selected topic model outputs from the Latent Dirichlet allocation (LDA) on patient provided input data. Stemmed words are expanded for clarity. Topic headings are interpreted by a user of the data processing system 200. As previously stated, feature data can be found by asking patients (e.g., pregnant and postpartum women, in this case) to describe their recent activities, interactions, and feelings. A few multiple choice questions about their past day are asked. Ground truth responses on depression and intimate partner violence are collected, and the sentiment analysis is used to find positive and negative connotations of text from data dictionaries. Latent Dirichlet Allocation and latent semantic indexing are used to find the topics, or groups of words often co-occurring. A LASSO regression is used to find smallest number of predictive features against depression and IPV measures.

Returning to FIG. 2, the feature transform logic engine 240 transforms the feature vector 220 into inputs for the machine learning engine 250. For example, the feature transform logic 240 can normalize the features of the feature vector 220 to values that can be recognized by the machine learning logic 250. For example, the feature vector 220 can be transformed into activation inputs for a neural network. In some implementations, the machine learning engine 250 includes a support vector machine. In some implementations, the machine learning engine 250 includes a convolutional neural network (CNN). In some implementations, the features of the feature vector are transformed into values between 0 and 1 through a non-linear transformation, where the normalized value represents an activation level for the neural network, and where the normalized scale is a non-linear representation of the values of the features before the normalization process. The values to which the features are transformed can depend on a type of machine learning engine 250 being used, and the weighting scheme associated with the machine learning engine 250.

The machine learning engine 250 is configured to receive the normalized features of the feature vector 220 and computes classification data 260, such as through a deep learning process. For example, neural network logic can include a long short-term memory (LSTM) neural network, which tracks dependencies between features of the feature vector 220. Other recurrent neural networks can be used. Other machine learning classifiers can be used as well.

The feature classifier data 260 includes one or more output values $<y_1 \ldots y_n>$ of the machine learning engine 250. For example, each output can be a classification value for one or more features of the feature vector 220. Each value of the classifier data 260 can indicate whether a health risk is represented or not represented in the features of the input data.

The classifier data 260 is sent to a prediction engine 270. The prediction engine 270 is configured to assign probabilities to one or more health risks as being present for the patient. The prediction data 280 shows the likelihood that each of one or more health risks is present for the patient. The collection of health risks and their associated probabilities of the probabilities data 280 can together be used to determine if the patient has a disease or other health condition. For example, if a user is showing health risks including high anxiety, high apathy, etc., a health condition of depression can be identified for that patient. The health condition data 290 and/or the probabilities data 280 can be presented to the patient or used to trigger a remediation action, as previously described.

Figure 3C:
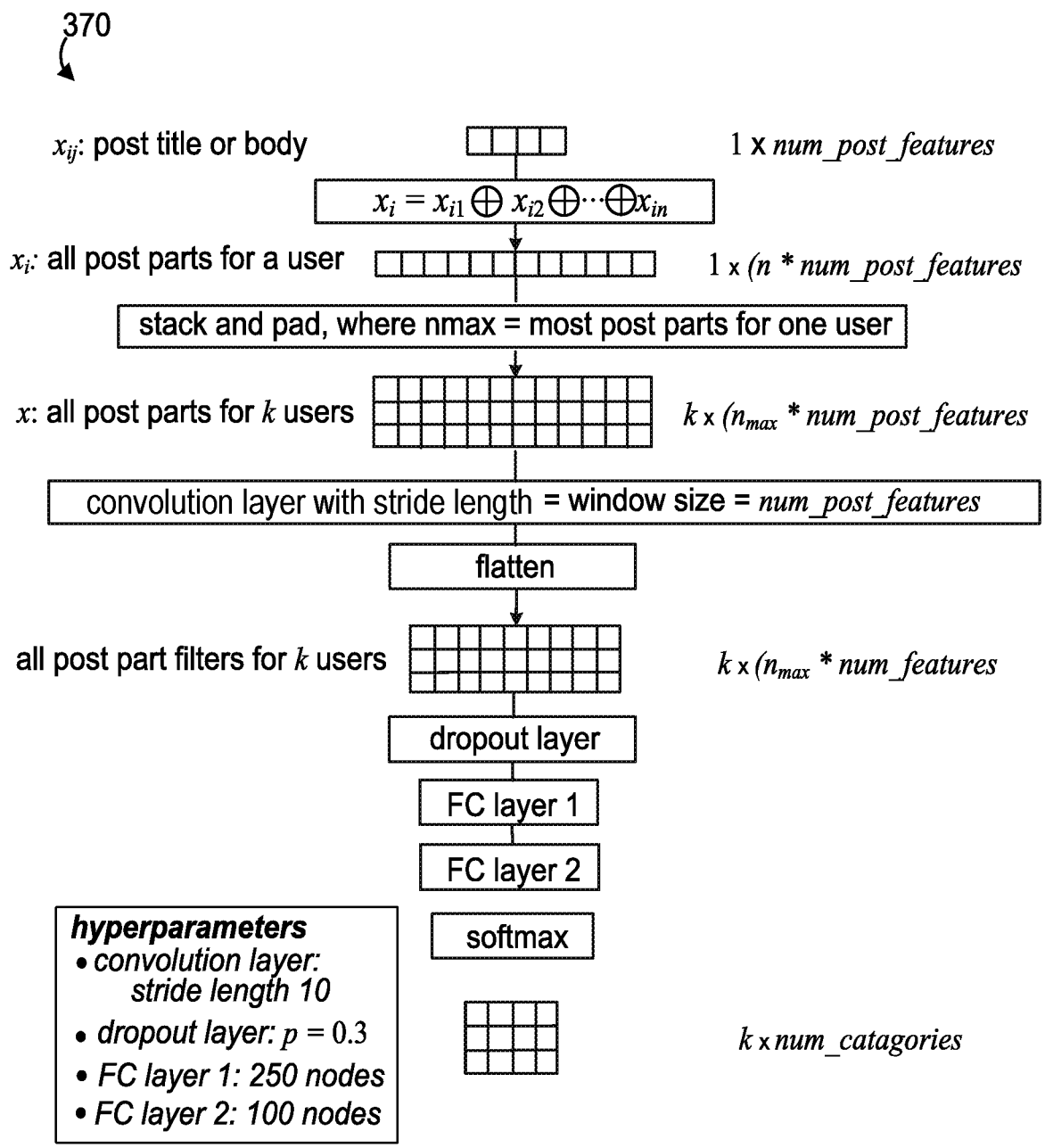
FIG. 3C shows an example of machine learning logic.

Turning briefly to FIG. 3C as a specific implementation, in some implementations, convolutional neural networks such as network 370 form the basic architecture for the machine learning engine 250. To generate the feature vector 220, the data processing system 200 is configured to concatenate word embeddings for each word in an entry, then concatenate these embedding sequences for all entry in order of occurrence.

The discussion with respect to FIGS. 3C-5B represents a particular, simplified example provided for illustrative purposes. This example shows how a particular implementation of the data processing system 200 can be configured to operation on particular data. In practice, more complex approaches can be used for generating features and classification of the features. For example, while a CNN is shown, the data processing system 200 can execute other machine learning logic for the classification engine. This example is intended to remove some implementation details to provide a concise, illustrative example of application of the data processing system 200 previously described.

In this example, the data processing system 200 can be configured to transform all entries by a patient into a two-dimensional array of dimension num_total_words*embedding size. For the CNN, filter parameters that must be trained are then a window_size*embedding_size*num_filters. Given the small size of the expert-annotated dataset, ways to reduce the number of features that the data processing system 200 trains are described.

In this example, the data processing system 200 uses entry-level (e.g., input data level) features. In this dataset the entry body field (of a journal entry) is often empty, presumably when the entry comprises only an image or other embedded media. As a result, features 220 are robust to this variation. In all subsequent models, each entry component (title or body) is represented as a one-dimensional vector of size num_entry_features. Calling each such 1D vector $x_{ij}$, the data processing system 200 chronologically concatenates these vectors for each post title and non-empty body for patient i into a longer 1-D vector: $x_i = x_{i1} \oplus x_{i2} \oplus \ldots \oplus x_{in}$.

Thus, the data processing system 200 represents each patient with the concatenated vector of all entries up to that time point post features from posts 1:n, where n is the patient's total number of post titles and non-empty post bodies. The resulting vector for a patient i has shape 1*(n_num_post_features). Patients are then batched for quicker training. Each patient vector is padded to the length of the longest one, resulting in a batch of k user vectors having shape $k*(n_{max}\_num\_entry\_features)$. Masking prevents back-propagation of weights to padding vectors.

The data processing system 200 uses sets of language features as the summary of each entry by a patient, then concatenates these features from all of a patient's entries. In order to maintain cross-entry context while reducing the number of features, the first model considers only features from the 'affect' category. Using just these sentiments appears likely to predict self-destructive mental state. Subsequent models use all 45 features provided in the LIWC dictionary, which can be the data dictionary 215.

The data processing system 200 can use a convolutional neural network as machine learning logic 250 for applying to this 1-D sequence of LIWC features 220 (e.g., without an extra feature transform 240). For example, the network can include the keras implementation of a one-dimensional CNN, setting both stride length and window size equal to num_entry_features and using num_filters=10 filters. This structure means that each window looks at LIWC features from a single entry title or body, and extracts relationships between these features into 10 filter representations. The model forgoes pooling in favor of maintaining independent information about each entry. Thus, after convolution, the batch of k users with max number of entry $n_{max}$ has shape $k*(n_{max}$ num_filters). Convolution can be followed by a dropout layer setting 30% of input units to 0 at any given time step, intended to reduce overfitting. In this example, the next two layers can be fully connected, with 250 and 100 nodes, respectively, and rectified linear activation functions. Thus, after passing through the second linear layer, the data has shape k*100. Finally, labels of the classifier data 260 are generated by a softmax output layer. Training seeks to minimize cross entropy, and uses 10-fold cross-validation (CV) on the training set.

Figure 4:
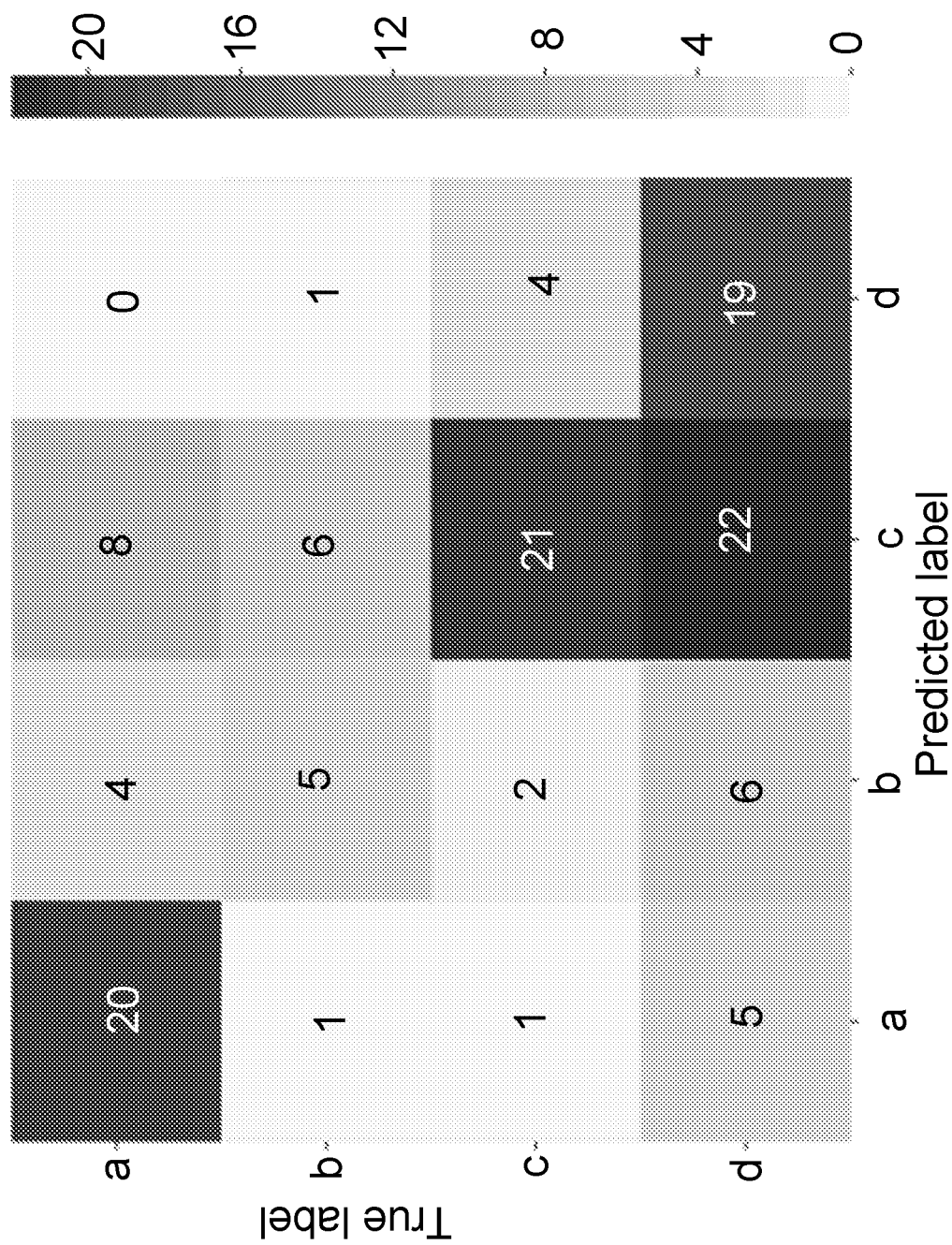
FIG. 4 shows a confusion matrix.

Several examples of the model can be applied. An 'affect-only' model uses the four affect categories relating to negative sentiment: 'negative affect,' 'anger,' 'anxiety,' and 'sadness'. This subset can be selected as a reasonable approximation of negative valence, and can be tested for predictive performance without broader information. A 'primary' model differs from the affect-only model by incorporating all 45 LIWC categories as entry features. A 'balanced classes' model includes custom weights corresponding to the penalty incurred while misclassifying each class. Larger weights are provided for the underrepresented 'low risk' and 'moderate risk' classes to force the model to pay more attention to these categories while training. Last, a 'leave none out' model uses all available data for training. In the primary and balanced models, it was clear that while training set performance continues to improve, development set performance levels off somewhere around 150 epochs. That is, cross-validation results were optimized at epoch 235 for the primary model, and 67 for the balanced classes model. Taking the average, this system uses the model state after epoch 150 to predict test set results. FIG. 4 shows a confusion matrix 400 for the test set from the best-performing model.

One evaluation metric is the resulting macro-averaged F1 score of our models. A report averages on a set-aside development set are shown in table one (see Table 1). Macro-averaged F1 scores on an unseen test set are also available in Table 2.

TABLE 1

Average performance of the models in 10-fold cross-validation on the training set.

| Model | Precision | Recall | F1 |
| --- | --- | --- | --- |
| CNN + GloVe vectors | 0.55 | 0.43 | 0.42 |
| Affect-only CNN + LIWC | 0.53 | 0.47 | 0.49 |
| Primary: CNN + all LIWC | 0.65 | 0.55 | 0.56 |

Table 2 shows the performance of the models by macro-averaged F1 on the test set. 'Full F1' indicates score across four classes, while 'flagged' and 'urgent' F1 reflect binary splits between no/some risk and non-severe/severe risk, respectively. All three submitted models use a convolutional network plus all LIWC features.

TABLE 2 performance of the models by macro-averaged F1 on the test set.

| Model | Full F1 | Flagged F1 | Urgent F1 |
| --- | --- | --- | --- |
| Primary | 0.37 | 0.88 | 0.77 |
| Leave none out | 0.50 | 0.90 | 0.82 |
| Balanced classes | 0.41 | 0.90 | 0.80 |

With the convolutional network model, using word embeddings in a convolutional neural network, the data processing system 200 has a can have a macro-averaged F1 score of 0.42. This model generally overfits the data; it performs exceptionally well on the training data (F1=0.95) and less well on development data (F1=0.42). This overfitting is expected, since the size of the dataset is insufficient to train large models.

The high overfitting and the model's inability to further learn from the dataset encourage focus on simpler models, and to thoughtfully select features. The best performing models use LIWC features at the entry level, concatenated by user, and run through a one-dimensional CNN with stride length and window size equal to the number of features.

Example results of model tests are described. For the affect-only model, when representing each entry as a vector of LIWC affect features, the base model achieves an F1-score of 0.47 in cross-validation. There is a significant discrepancy between the model's performance on seen/unseen data, indicating that the model overfits. Experiments with hyper-parameters like dropout and number of filters were performed, finding that a model with 10 filters and 0.3 dropout probability outperforms all our previous models with a macro-averaged CV F1-score of 0.49.

On studying the performance of the model in this example, the behavior is not uniform across all classes. The model does well in labeling 'no risk' and 'severe risk,' health risks, but performs less well in trying to label the intermediate risk categories.

The primary model uses variations to improve features provided while still minimizing parameters trained. For the primary model, all 45 LIWC category features are provided by the data processing system 200 to a CNN of the same structure. In macro-averaging pairwise AUC scores on the development set, this model scores 0.76. On the test set, the model's macro-averaged F1 is 0.37. A random guessing strategy weighted by label frequency would yield F1=0.25. For the balanced classes model, this change boosts the model's CV performance on our development set to an F1 score of 0.57, with a macro-averaged AUC score on the development set of 0.78. This model performs more uniformly across the four classes than the previous model, resulting in a slightly better score on the unseen test set, F1=0.40.

For the leave none out model, the model is trained on the entire training dataset available for Task A, stopping after 150 epochs. This model achieves the highest score on the test set, which is a macro-averaged F1-score of 0.50. This compares favorably with the best-scoring system, which F1-score is 0.53. This model achieves high F1-scores (0.90 and 0.82 respectively) for 'flagged' and 'urgent' tasks.

This model's final confusion matrix 400 is shown in FIG. 4. We find that this model is best at identifying the 'no risk' and 'moderate risk' patients.

Primary and balanced classes models perform similarly, with a difference in F1 scores of about 0.03. The latter model is slightly more effective because its higher weights for the intermediate categories counteracted those labels' lower representation in the training set. This is borne out in the model's slightly better performance on those classes: it categorizes 1 of 'low risk' and 10 'moderate risk' users correctly, whereas the 'primary' model is right about 13 and 8 of such users, respectively. Macro-averaged F1 as the primary metric means that even this slight improvement is significant when comparing the two models. Because it was trained for longer, the 'primary' model was more over-fitted to the training data. Because we use 10-fold cross-validation to train these models, both these models are trained using 90% of the training data; this missing 10% of data is the primary reason that the leave-none-out model outperforms both of these models. A larger training dataset allows the model to "observe" more data, which helps both with getting more training data for under-represented classes (e.g. low and moderate risk) and with generalizing better on all unseen data.

Figure 5A:
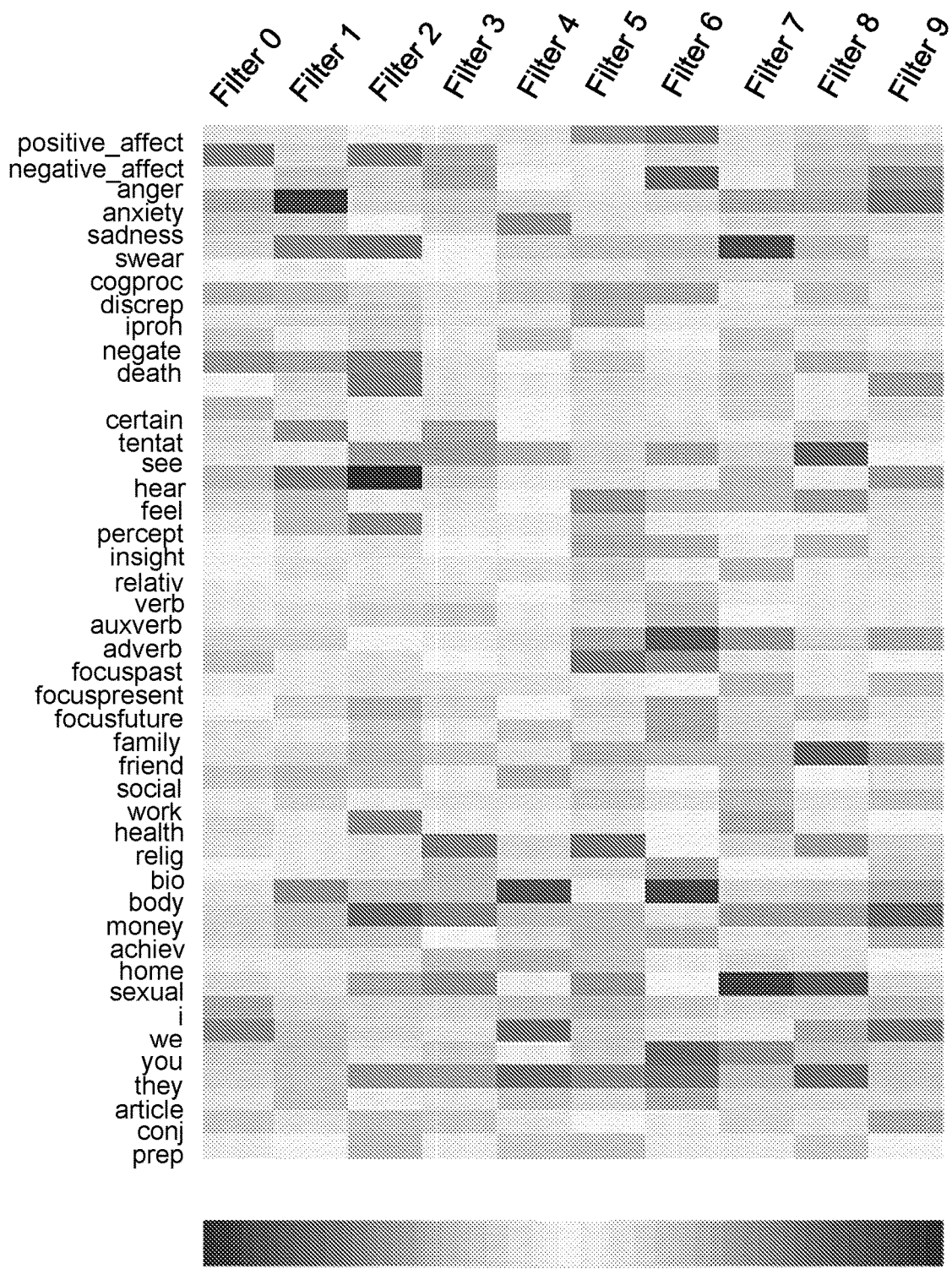
FIGS. 5A-5B show examples of filters.

In FIG. 5A, a plot 500 of the learned convolutional layer weights from the final model with respect to the input LIWC feature categories is shown. Each filter is activated (or deactivated) by a subset of LIWC features. Each filter focuses on learning presence or absence of a particular character trait (or 'sentiment') from each entry. For instance, filter 9 is inversely associated with money, anxiety, and 'we,' indicating that someone describing his or her stress around money would have a negative activation for Filter 9. Seeing a stronger association between Filter 9 and 'no risk,' it can be determined that users who are not at risk are less likely to be preoccupied with their financial troubles on r/SW.

Figure 5B:
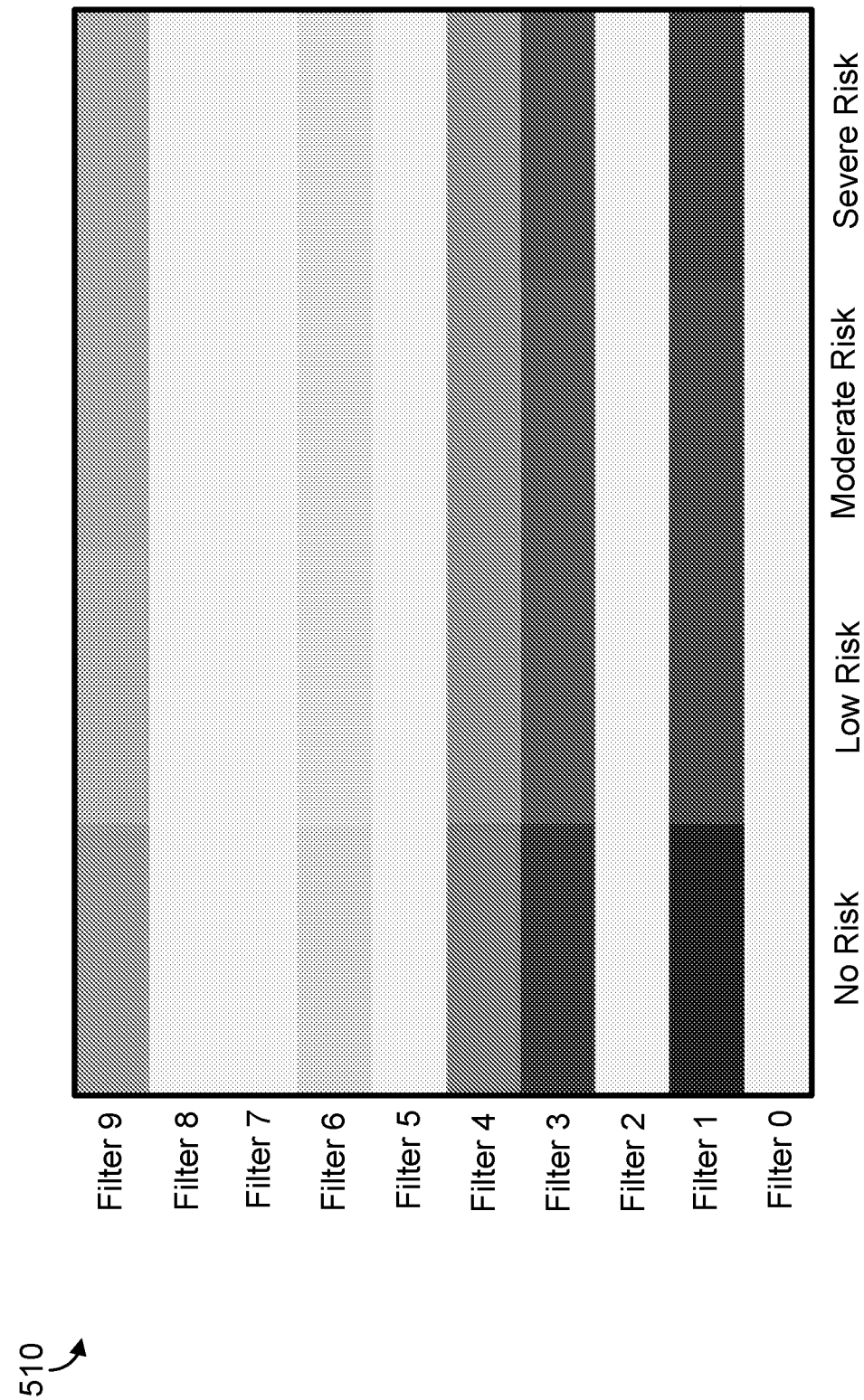

While not all subsets are clear, there are some patterns. For instance, Filter 2 has the highest positive weights for 'hear,' 'negative affect,' 'death,' 'percept,' and 'see.' A user activating this filter is preoccupied with how he or she is perceived, and is also considering death (whether their own or that of a loved one). This filter may indicate both a feeling of being observed, perhaps stigmatized, and an experience of suicidal ideation. FIG. 5B shows a graph 510 including strengths of average alignment between filters and the four classes.

Figure 6A:
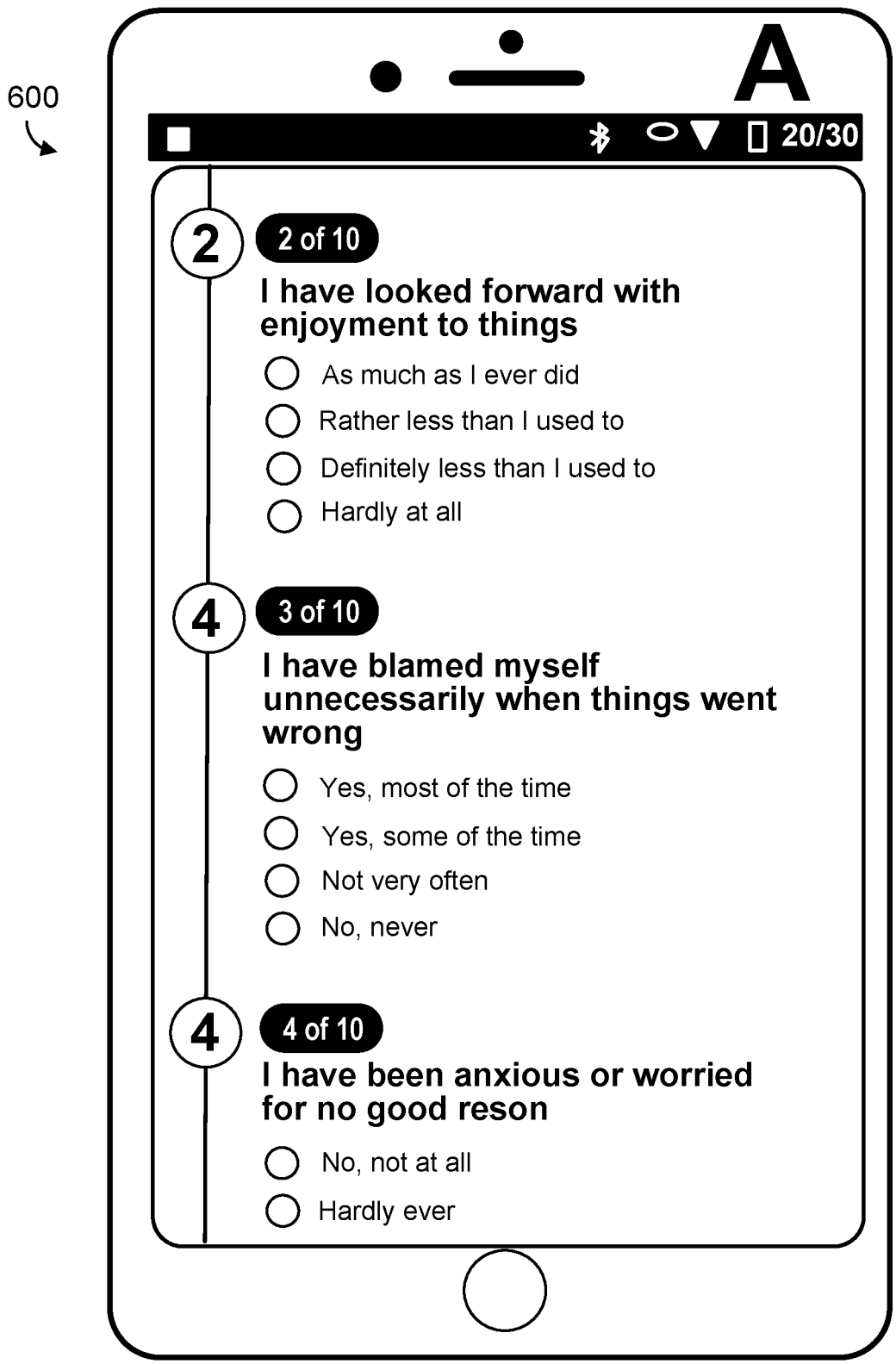
Figure 6B:
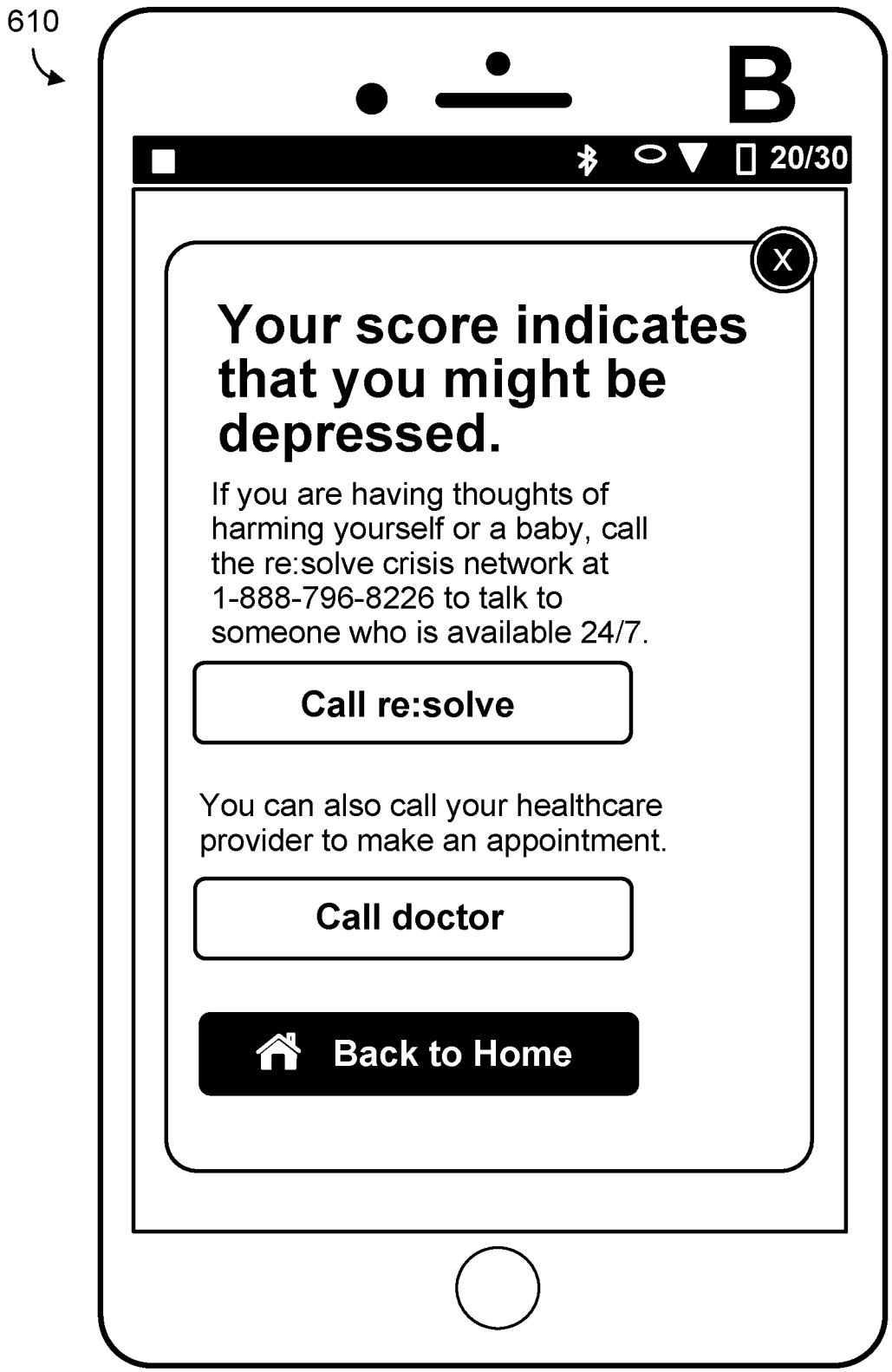
Figure 6C:
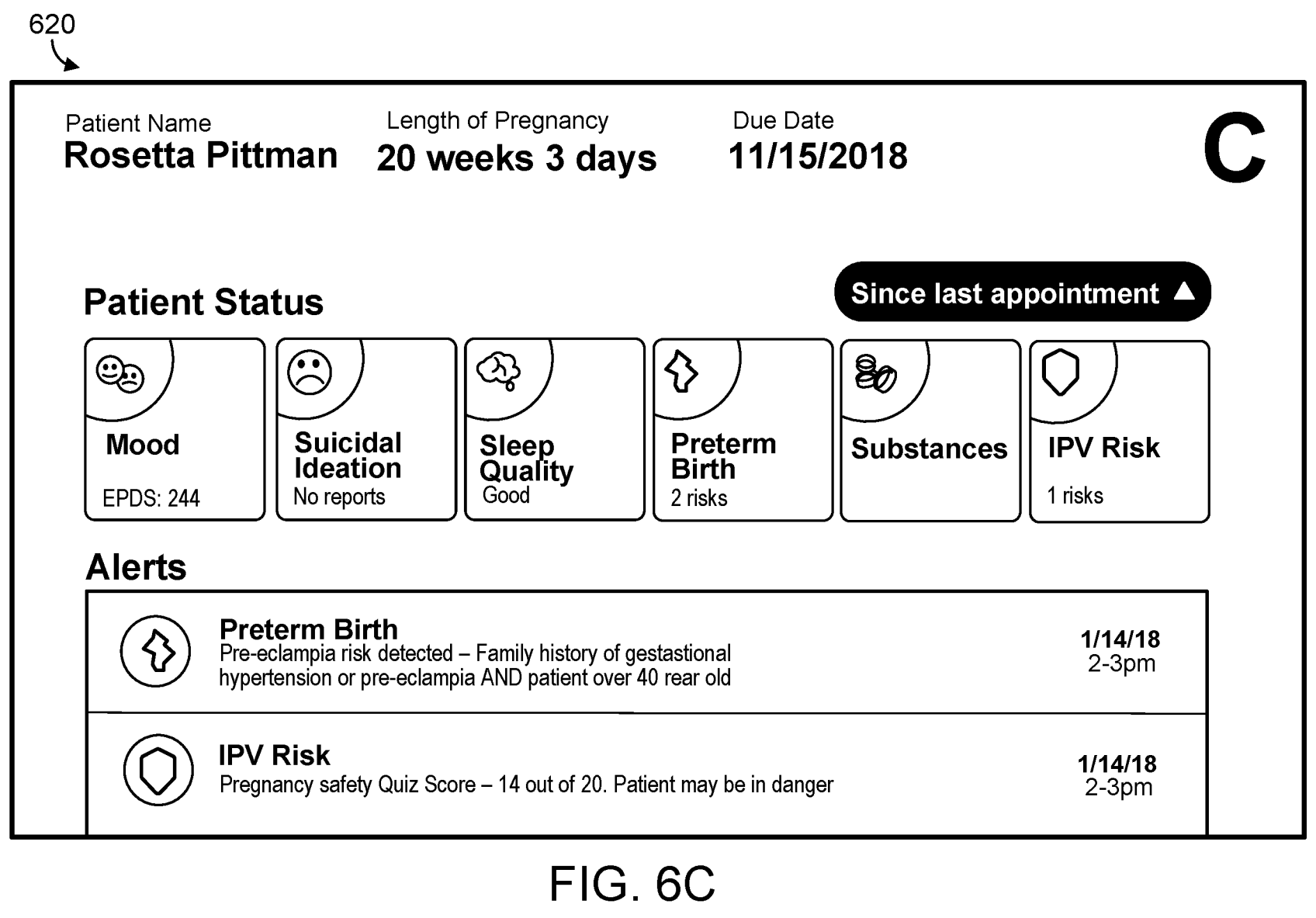

Turning to FIG. 6A-6C, user interfaces 600, 610, and 620 are shown. FIG. 6A shows interface 600 for how input data 205 are collected from a patient using a questionnaire. In response to inputting data, a patient can receive feedback, as shown by user interface 610 in FIG. 6B. FIG. 6C shows a user interface 620 that reports patient status data back to a medical service provider (or other caretaker or observer). For example, interface 620 can be provided to a therapist or a doctor. The data can be transmitted from the data processing system 200 to a device of the medical service provider, e.g., over network 130. This can allow a health service provider to quickly, accurately, and indirectly detect a health risk, such as depression during the peripartum period, providing an actionable response in real-time, and accelerating the discovery and treatment of issues as they arise.

In an example test of the data processing system 200, two waves of survey data were collected, one with 239 female U.S. residents of reproductive age (18-45 years), and one with 178 pregnant women and 131 women in the postpartum period. Women were asked open-ended questions, e.g., "What events have most impacted your mood in the past 24 hours?" and multiple-choice questions, e.g., "How would you describe your mood in the past 24 hours (very poor=1 to very good=5)?" as well as established psychometric measures of wellbeing, including the EPDS. To predict EPDS scores from our sample's open-ended responses, the methods described above in relation to FIGS. 1-6C were used. By running two of these algorithm types on the same data set, a set of unique scores were generated from the open-ended text and were entered into a penalized logistic regression model of depression, using a threshold of EPDS score >13. Table 3 presents initial results.

TABLE 3

Results of NLP approaches.

| | | Test set | |
| Risk | Feature class | $R^2$ | AUC |
| --- | --- | --- | --- |
| EPDS score >13 | Sentiment | .09 | .72 |
| | LDA topics | .02 | .60 |
| | All NLP | .07 | .74 |

Table 3 shows R2 and Area Under the ROC curve (AUROC) for depression by each of the NLP approaches across U.S. reproductive-aged women. EPDS >13 indicates meaningful possibility to high probability of clinical depression.

Using only sentiment, the test set AUROC is 0.72, indicating fair ability to separate those with and without depression using the effect of their natural language. As a comparison, the established PHQ-2 measure of depression has an AUROC of 0.84. Using only topics has an AUROC of 0.60. Combining all three NLP techniques gives an AUROC of 0.74, a performance close to the PHQ-2, but elicited without ever asking explicitly about depression. While the sentiment of language has the largest association with depression of the three approaches is shown, one key finding here is that there is no single feature for deducing depression from language. Each of the different model inputs captures a different aspect of a woman's language; each aspect of a woman's language can be effectively used to predict depression risk. These results reflect natural language captured at a single time point.

We have determined the relationship between EPDS scores and specific topics mentioned in daily journals, extracted through a natural language processing technique called Latent Dirichlet Allocation (LDA). LDA models each journal entry as a probabilistic combination (mixture) of topics. For example, an entry about pregnancy might include topics like childbirth, breastfeeding, and depression. Each of those topics is associated more with some words (childbirth and labor; breastfeeding and nutrition; depression and anxiety) than others (guns, farms, airplanes). Three types of LDA models are used: 1) LDA models constructed solely on daily journal entries, 2) pre-trained LDA models constructed from large text corpora, such as Twitter's 27B word corpus and the 6B word Wikipedia+Gigaword corpus, and 3) combinations of pre-trained LDA models with models trained on journal entries. Regularized logistic regression is used to determine whether some of those topics are more likely to appear in the journal entries of depressed versus non-depressed women.

The sentiment expressed in daily journal entries and the EPDS scores is also analyzed. Sentiment analysis characterizes each word as expressing either a positive or negative sentiment. Quantification of the positive and negative sentiments expressed is done using sentiment and deep neural network vector space models of natural language lexica. The total positive and negative sentiment in each journal entry is used to model EPDS scores.

Figure 7:
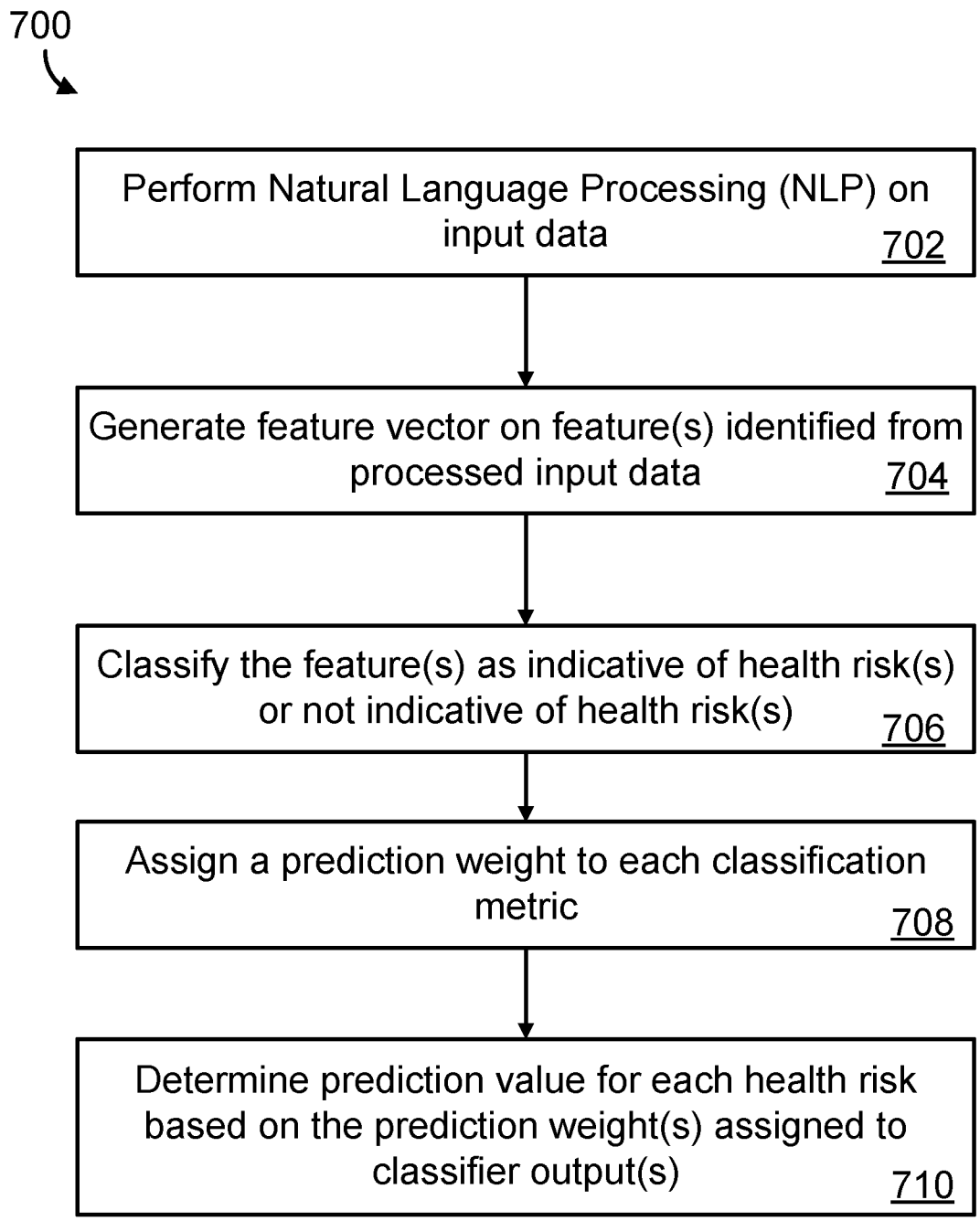
FIG. 7 shows a flow diagram.

FIG. 7 shows an example of a process 700 for detecting health risks and causing treatment responsive to the detection, such as by data processing system 200 of FIG. 2. The data processing system 200 is configured to perform (702) a Natural Language Processing (NLP) on input data received from one or more input sources. In some implementations, the NLP of the input data is performed by the input source. The input source can include a detection device (e.g., detection device 110 of FIG. 1) configured to receive text data. The text data can be in the form of comments, social media posts, audio data, journal entries through a provided user interface, and so forth as previously described. The data processing system 200 is configured to generate (704) a feature vector on feature(s) identified from processed input data. The feature vector can include one or more features identified from the input data. The feature vector is configured for inputting into machine learning logic, such as one or more neural networks. The feature vector can include activation values or parameters. The data processing system 200 is configured to classify (706) the feature(s) as indicative of health risk(s) or not indicative of health risk(s). The data processing system 200 can use the machine learning logic to perform this classification. In some implementations, each feature is classified as associated with a particular health risk or not associated with a particular health risk. For example, each feature can be associated with a list of classification metrics for each of the health risks being tested. The data processing system 200 is configured to assign (708) prediction weights to the classification metrics for the features that were classified by the machine learning logic of the classification engine. For example, the prediction engine can determine that a particular health risk was identified for most of the features of the feature vector. The prediction engine can associate a high weight to the classification metrics for that health risk based on the corroboration observed for different features of the input data. The prediction engine determines (710) a prediction value for each health risk based on the prediction weight(s) assigned to classifier output(s). In other words, the prediction engine determines a prediction value for each health risk based on the weights for the classification metrics. The prediction engine can suggest one or more health risks are present for the patient. The data processing system 200 can suggest one or more related conditions or diseases based on the health risks observed, and generate an alert, alarm, notification, etc. to be observed by the patient and/or a medical service provider of the patient. For example, the alert can be sent to a patient's computing device or a system of the medical service provider.

Some implementations of subject matter and operations described in this specification can be implemented in digital electronic circuitry, or in computer software, firmware, or hardware, including the structures disclosed in this specification and their structural equivalents, or in combinations of one or more of them. For example, in some implementations, the monitoring system 102, the client device 112, and the computing system 114 can be implemented using digital electronic circuitry, or in computer software, firmware, or hardware, or in combinations of one or more of them. In another example, the processes 500 and 600, can be implemented using digital electronic circuitry, or in computer software, firmware, or hardware, or in combinations of one or more of them.

Some implementations described in this specification (e.g., the query response module 104, the data structure module 106, etc.) can be implemented as one or more groups or modules of digital electronic circuitry, computer software, firmware, or hardware, or in combinations of one or more of them. Although different modules can be used, each module need not be distinct, and multiple modules can be implemented on the same digital electronic circuitry, computer software, firmware, or hardware, or combination thereof.

Some implementations described in this specification can be implemented as one or more computer programs, i.e., one or more modules of computer program instructions, encoded on computer storage medium for execution by, or to control the operation of, data processing apparatus. A computer storage medium can be, or can be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate physical components or media (e.g., multiple CDs, disks, or other storage devices).

The term "data processing apparatus" encompasses all kinds of apparatus, devices, and machines for processing data, including by way of example a programmable processor, a computer, a system on a chip, or multiple ones, or combinations, of the foregoing. In some implementations, the query response module 104 and/or the data structure module 106 comprises a data processing apparatus as described herein. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed for execution on one computer or on multiple computers that are located at one site or distributed across multiple sites and interconnected by a communication network.

Some of the processes and logic flows described in this specification can be performed by one or more programmable processors executing one or more computer programs to perform actions by operating on input data and generating output. The processes and logic flows can also be performed by, and apparatus can be implemented as, special purpose logic circuitry, e.g., an FPGA (field programmable gate array) or an ASIC (application specific integrated circuit).

Processors suitable for the execution of a computer program include, by way of example, both general and special purpose microprocessors, and processors of any kind of digital computer. Generally, a processor will receive instructions and data from a read only memory or a random access memory or both. A computer includes a processor for performing actions in accordance with instructions and one or more memory devices for storing instructions and data. A computer may also include, or be operatively coupled to receive data from or transfer data to, or both, one or more mass storage devices for storing data, e.g., magnetic, magneto optical disks, or optical disks. However, a computer need not have such devices. Devices suitable for storing computer program instructions and data include all forms of non-volatile memory, media and memory devices, including by way of example semiconductor memory devices (e.g., EPROM, EEPROM, flash memory devices, and others), magnetic disks (e.g., internal hard disks, removable disks, and others), magneto optical disks, and CD-ROM and DVD-ROM disks. The processor and the memory can be supplemented by, or incorporated in, special purpose logic circuitry.

To provide for interaction with a user, operations can be implemented on a computer having a display device (e.g., a monitor, or another type of display device) for displaying information to the user and a keyboard and a pointing device (e.g., a mouse, a trackball, a tablet, a touch sensitive screen, or another type of pointing device) by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

A computer system may include a single computing device, or multiple computers that operate in proximity or generally remote from each other and typically interact through a communication network. Examples of communication networks include a local area network ("LAN") and a wide area network ("WAN"), an inter-network (e.g., the Internet), a network comprising a satellite link, and peer-to-peer networks (e.g., ad hoc peer-to-peer networks). A relationship of client and server may arise by virtue of computer programs running on the respective computers and having a client-server relationship to each other.

Figure 8:
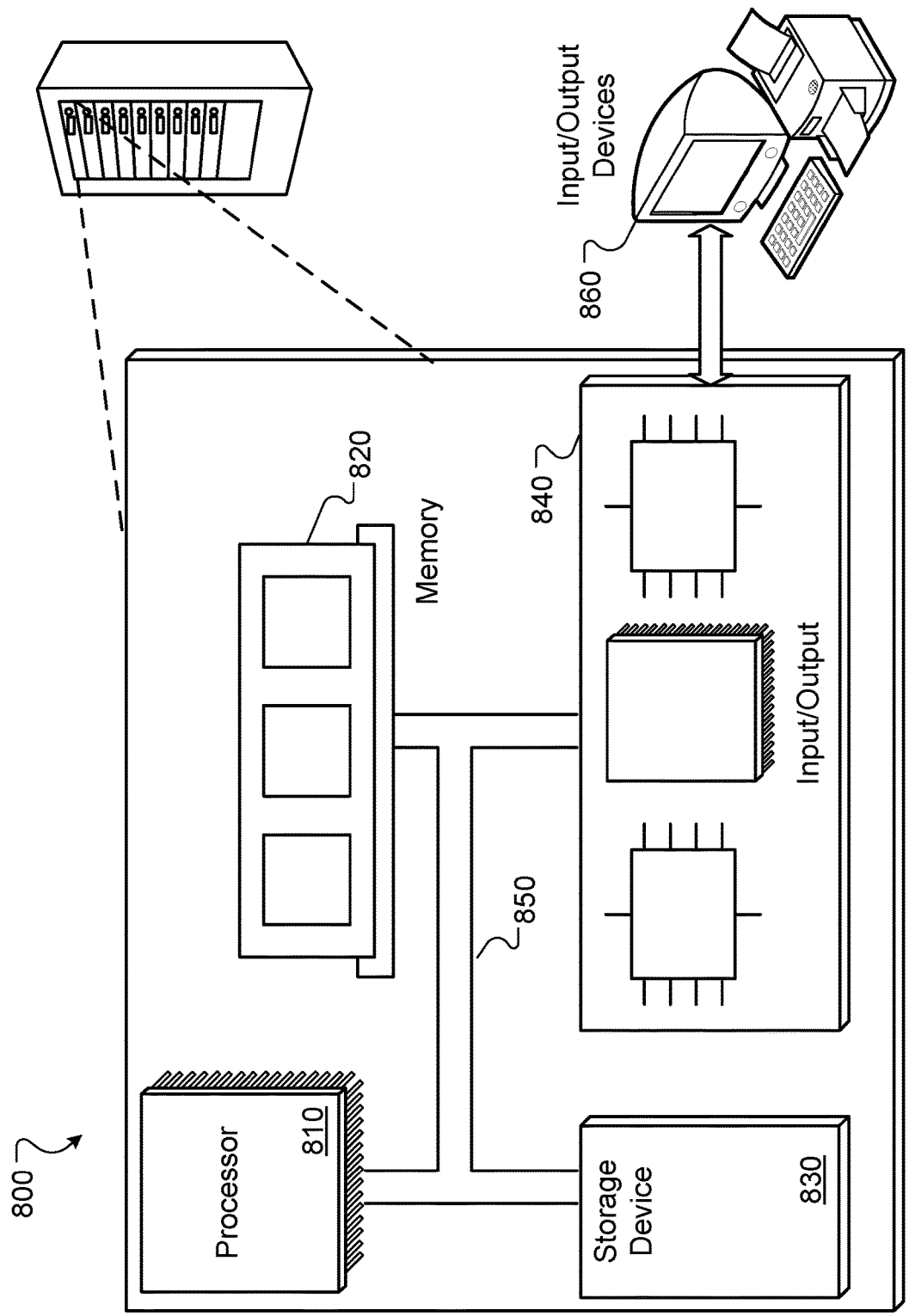
FIG. 8 is a diagram of an example computing system.

FIG. 8 shows an example computer system 800 that includes a processor 810, a memory 820, a storage device 830 and an input/output device 840. Each of the components 810, 820, 830 and 840 can be interconnected, for example, by a system bus 850. The processor 810 is capable of processing instructions for execution within the system 800. In some implementations, the processor 810 is a single-threaded processor, a multi-threaded processor, or another type of processor. The processor 810 is capable of processing instructions stored in the memory 820 or on the storage device 830. The memory 820 and the storage device 830 can store information within the system 800.

The input/output device 840 provides input/output operations for the system 800. In some implementations, the input/output device 840 can include one or more of a network interface device, e.g., an Ethernet card, a serial communication device, e.g., an RS-232 port, and/or a wireless interface device, e.g., an 802.11 card, a 3G wireless modem, a 4G wireless modem, a 5G wireless modem, etc. In some implementations, the input/output device can include driver devices configured to receive input data and send output data to other input/output devices, e.g., keyboard, printer and display devices 860. In some implementations, mobile computing devices, mobile communication devices, and other devices can be used.

While this specification contains many details, these should not be construed as limitations on the scope of what may be claimed, but rather as descriptions of features specific to particular examples. Certain features that are described in this specification in the context of separate implementations can also be combined. Conversely, various features that are described in the context of a single implementation can also be implemented in multiple embodiments separately or in any suitable sub-combination.

A number of embodiments have been described. Nevertheless, it will be understood that various modifications may be made without departing from the spirit and scope of the data processing system described herein. Accordingly, other embodiments are within the scope of the following claims.

What is claimed is:

1. A data processing system for identifying treatment responsive to a health risk determined from feature data provided by one or more networked data sources, the data processing system comprising one or more processors configured to perform operations comprising:

generating a feature vector based on a natural language processing (NLP) of input data that is unstructured and representing one or more words provided by a user, with the feature vector comprising one or more features representing one or more health risk factors, the generating comprising:

applying a set of different NLP models to the input data, each of the different NLP models configured to generate a subset of features for the feature vector;

selecting the one or more features of the feature vector, from the subset of features of each of the different NLP models, based on cross-validation of different subsets of training data when training machine learning logic;

classifying, using the machine learning logic that is trained on additional unstructured input data, each of the one or more features of the feature vector to generate a classification metric indicating, for each of the one or more features, that the feature is indicative of a health risk or not indicative of a health risk, the machine learning logic being trained by performing operations including:

accessing training data that associates words or phrases, of the additional unstructured input data, with a set of features including the one or more features of the feature vector, the one or more features each being labeled with a health risk severity level; and training the machine learning logic based on the cross-validation of the different subsets of the training data; and generating a prediction value indicative of a predicted likelihood of each health risk factor of the one or more health risk factors by performing operations comprising:

assigning, to one or more of the classification metrics, a prediction weight; and determining the prediction value for each health risk factor based on the assigned prediction weights.

2. The data processing system of claim 1, the operations further comprising generating data for a graphical user interface configured for displaying, when rendered on a client device, one or more prompts to enter the input data, the prompts comprising open-ended queries.

3. The data processing system of claim 2, wherein the graphical user interface is configured to display a determined health condition for the user determined by comparing prediction values for one or more of the health risk factors to threshold values.

4. The data processing system of claim 1, the operations further comprising generating data for a graphical user interface comprising a user status report, wherein data for the graphical user interface is transmittable to a remote device for review by a medical service provider.

5. The data processing system of claim 1, wherein the natural language processing is used to generate the features for risk classification.

6. The data processing system of claim 1, wherein a feature of the feature vector represents a demographic of the user and other user-specific data.

7. The data processing system of claim 1, the operations further comprising selecting a health condition for a user in response to a given prediction value for a given health risk factor exceeding a threshold value.

8. The data processing system of claim 1, wherein the health risks include one or more mental and behavioral health risks consisting of a risk of depression, a risk of suicidality, a risk of self-harm, a risk of harm from others including intimate partner violence, and a risk of an addiction.

9. The data processing system of claim 1, wherein the input data comprises audio data received through a microphone.

10. A method for identifying treatment responsive to a health risk determined from feature data provided by one or more networked data sources, the method comprising:

generating a feature vector based on a natural language processing (NLP) of input data that is unstructured and representing one or more words provided by a user, with the feature vector comprising one or more features representing one or more health risk factors, the generating comprising:

applying a set of different NLP models to the input data, each of the different NLP models configured to generate a subset of features for the feature vector;

selecting the one or more features of the feature vector, from the subset of features of each of the different NLP models, based on cross-validation of different subsets of training data when training machine learning logic;

classifying, using the machine learning logic that is trained on additional unstructured input data, each of the one or more features of the feature vector to generate a classification metric indicating, for each of the one or more features, that the feature is indicative of a health risk or not indicative of a health risk, the machine learning logic being trained by performing operations including:

accessing training data that associates words or phrases, of the additional unstructured input data, with a set of features including the one or more features of the feature vector, the one or more features each being labeled with a health risk severity level; and training the machine learning logic based on the cross-validation of the different subsets of the training data;

assigning, to one or more of the classification metrics, a prediction weight; and determining the prediction value for each health risk factor based on the assigned prediction weights.

11. The method of claim 10, further comprising generating data for a graphical user interface configured to display, when rendered on a client device, one or more prompts to enter the input data, the prompts comprising open-ended queries.

12. The method of claim 11, wherein the graphical user interface is configured to display a determined health condition for a user determined by comparing prediction values for one or more of the health risk factors to threshold values.

13. The method of claim 10, further comprising generating data for a graphical user interface comprising a user status report, wherein data for the graphical user interface is transmittable to a remote device for review by a medical service provider.

14. The method of claim 10, wherein the natural language processing is used to generate features for risk classification.

15. The method of claim 10, wherein a feature of the feature vector represents a demographic of the user and other user-specific data.

16. The method of claim 10, further comprising selecting a health condition for the user in response to a given prediction value for a given health risk factor exceeding a threshold value.

17. The method of claim 10, wherein the health risks include one or more mental and behavioral health risks consisting of a risk of depression, a risk of suicidality, a risk of self-harm, a risk of harm from others including intimate partner violence, and a risk of an addiction.

18. The method of claim 10, wherein the input data comprises audio data received through a microphone.

19. A non-transitory computer readable medium storing instructions that are executable by one or more processors configured to perform operations comprising:

generating a feature vector based on a natural language processing (NLP) of input data that is unstructured and representing one or more words provided by a user, with the feature vector comprising one or more features representing one or more health risk factors, the generating comprising:

applying a set of different NLP models to the input data, each of the different NLP models configured to generate a subset of features for the feature vector;

selecting the one or more features of the feature vector, from the subset of features of each of the different NLP models, based on cross-validation of different subsets of training data when training machine learning logic;

classifying, using machine learning logic that is trained on additional unstructured input data, each of the one or more features of the feature vector to generate a classification metric indicating, for each of the one or more features, that the feature is indicative of a health risk or not indicative of a health risk, the machine learning logic being trained by performing operations including accessing training data that associates words or phrases, of the additional unstructured input data, with a set of features including the one or more features of the feature vector, the one or more features each being labeled with a health risk severity level; and training the machine learning logic based on the cross-validation of the different subsets of the training data;

assigning, to one or more of the classification metrics, a prediction weight; and determining the prediction value for each health risk factor based on the assigned prediction weights.

20. The non-transitory computer readable medium of claim 19, further comprising generating data for a graphical user interface configured to display, when rendered on a client device, one or more prompts to enter the input data, the prompts comprising open-ended queries.

* * * * *